United States Patent [19]

Pillot et al.

[11] Patent Number: 4,806,666

[45] Date of Patent: Feb. 21, 1989

[54] FUNCTIONAL 1,3-DIHYDROGENO DISILAZANES

[75] Inventors: Jean-Paul Pillot, Cestas; Eric Bacque, Talence; Jacques Dunogues, Talence; Claude Biran, Talence; Pierre Olry, Bordeaux, all of France

[73] Assignee: Societe Europeenne de Propulsion, Suresnes, France

[21] Appl. No.: 54,300

[22] Filed: May 26, 1987

[30] Foreign Application Priority Data

May 26, 1986 [FR] France .................. 86 07479

[51] Int. Cl.[4] .............................. C07F 7/10
[52] U.S. Cl. .................................. 556/412
[58] Field of Search ........................ 556/412

[56] References Cited

U.S. PATENT DOCUMENTS

| | | | |
|---|---|---|---|
| 3,253,008 | 5/1966 | Fink | 556/412 |
| 3,308,146 | 3/1967 | Merker | 260/448.2 |
| 3,393,218 | 7/1968 | Van Wazer et al. | 556/412 |
| 3,408,379 | 10/1968 | McVannel | 556/412 |
| 4,383,119 | 5/1983 | Pullukat | 556/412 |
| 4,404,153 | 9/1983 | Gaul | 556/412 X |
| 4,414,403 | 11/1983 | Schilling et al. | 556/430 |
| 4,540,803 | 9/1985 | Cannady | 556/412 |
| 4,612,383 | 9/1986 | Laine et al. | 556/412 |

FOREIGN PATENT DOCUMENTS

| | | | |
|---|---|---|---|
| 1334850 | 7/1963 | France | 556/412 X |
| 2163792 | 7/1973 | France | 556/412 X |

OTHER PUBLICATIONS

Drake et al., "J. Chem. Soc.", pp. 3617–3620, 1971.
Andrianov, Astakhin and Kochkin, *Chemical Abstracts*, 58, 9115a (1963).
Andrianov, Il'in, Talanov, Konstantinova and Kazakova, *Journal of General Chemistry of the USSR*, 47, 1608–1609 (1977).
*Inorganic Chemistry*, series one, vol. 4, pp. 149–150 (Aylett, ed., Buttersworth).
Noll, *Verlag Chemie GmbH*, pp. 43–44 (1968).
Semenova et al., *Chemical Abstracts*, 58, 9114h (1963).

*Primary Examiner*—Paul F. Shaver
*Attorney, Agent, or Firm*—Willian Brinks Olds Hofer Gilson & Lione, Ltd.

[57] ABSTRACT

The present invention relates to functional 1,3-dihydrogeno disilazanes of formula:

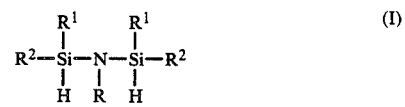

in which:

R and $R_1$, identical or different, represent an atom of hydrogen or a hydrocarbon such as an alkyl, alkenyl or alkynyl, cycloalkyl or cycloalkenyl, aryl, alkylaryl, alkenylaryl, alkynylaryl, arylalkyl, arylalkenyl or arylalkynyl radical, possibly functional, R also being able to represent a radical

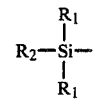

and $R_2$ represents an atom of halogen, an OR group or an $-NRR_1$ group, when R and $R_1$ are both hydrocarbon radicals.

12 Claims, No Drawings

FUNCTIONAL 1,3-DIHYDROGENO DISILAZANES

The present invention relates to functional 1,3-dihydrogeno disilazanes.

The products according to the invention are silazanes having the following formula:

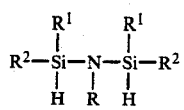

in which:

R and $R_1$, identical or different, each represent an atom of hydrogen or a hydrocarbon such as an alkyl, alkenyl or alkynyl, cycloalkyl or cycloalkenyl, aryl, alkylaryl, alkenylaryl, alkynylaryl, arylalkyl, arylalkenyl or arylalkynyl radical, possibly functional, R also being able to represent the radical

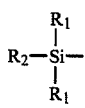

and $R_2$ represents an atom of halogen, an OR group or an $-NRR_1$ group, when R and $R_1$ are both hydrocarbon radicals.

Among the compounds of formula (I), particular mention will be made of those for which the symbols represent:

R an atom of hydrogen or an alkyl or alkenyl group with 1 to 4 carbon atoms;
$R^1$ an alkyl or alkenyl group with 1 to 4 carbon atoms;
$R^2$ an atom of chlorine.

Among compounds (I), the following will be mentioned by way of illustration:
1,3-dichloro 1,3-dimethyl disilazane;
1,3-dichloro 1,2,3-trimethyl disilazane;
1,3-dichloro 1,3-divinyl disilazane;
1,3-dichloro 1,3-divinyl 2-methyl disilazane.

The originality of these products lies in the fact that these disilazanes possess two atoms of silicon each bonded only to one carbon atom at maximum and that they therefore possess a functional group which is bonded thereto in addition to the hydrogeno and aminosilane functions.

The disilazanes of formula (I) may be prepared by action of an excess of chlorosilane $R^1R^2HSiCl$ on aminosilane $RN(SiMe_3)_2$ in the presence, or not, of a solvent such as pentane, cyclohexane, benzene, this list not being limiting, at a temperature allowing the formation of $Me_3SiCl$ whilst avoiding decomposition of the compound (I) formed, which temperature is generally between 0° and 130° C.

Compounds (I) may be isolated from the reaction medium by various known means and in particular by distillation generally under reduced pressure.

Compounds (I) have, up to the present time, never been described. They may have very different applications and in particular be used for making polycarbosilazanes, precursors of basic materials of silicon carbonitride.

The following Examples illustrate, in non-limiting manner, the products of formula (I) and a process for preparing said products.

Example 1

Hexamethyldisilazane (64.6 g) and methyldichlorosilane (184 g) are heated to reflux for 6 hours. After this time, the total disappearance of the hexamethyldisilazane is ascertained by nuclear magnetic resonance spectroscopy of the proton ($^1$HNMR). The compound (I) of formula Cl(Me)(H)SiNHSi(H)(Me)Cl is separated by distillation in vacuo (b.p./mmHg: 41° C./4); yield: 95%) and identified without ambiguity by conventional physico-chemical techniques (infrared and $^1$HNMR spectrometries, in particular). Stable at $-20°$ C., in an inert atmosphere, it decomposes very slowly at ambient temperature with formation, in particular, of ammonium chloride and reacts with water with considerable violence. It must therefore be conserved at low temperature, away from humidity, and preferably in an inert atmosphere, but may be employed without too considerable decomposition in a solvent medium, hot.

Example 2

Hexamethyldisilazane (16.14 g) and ethyldichlorosilane (51.62 g) are heated to reflux. After 4 hours, the $^1$HNMR spectrum of the medium shows the total disappearance of the hexamethyldisilazane.

The compound of formula $(HEtClSi)_2N$ (19.01 g) is then isolated by distillation under high vacuum, with a yield of 94% (b.p.$_{0.5}$=48° C.). Its structure is confirmed without ambiguity by NMR spectroscopy.

The disilazane is very sensitive to hydrolysis and decomposes slowly at 20° C. However, stored at $-20°$ C. in an argon atmosphere, it may be conserved for several months without too considerable degradation.

Example 3

Hexamethyldisilazane (11.7 g) and vinyldichlorosilane (36.85 g) are heated to reflux. After 6 hours, the hexamethyldisilazane was totally consumed, as demonstrated by $^1$HNMR spectroscopy.

Distillation under high vacuum of the reaction medium makes it possible to isolate a colourless liquid (b.p.$_{0.5}$=43° C.) identified as being $(HViClSi)_2NH$. The yield is 90% (12.92 g).

Conservation of this product at $-20°$ C. in an argon atmosphere, preserves its integrity for several months, limiting its degradation.

Example 4

After 3 hours of heating to reflux of a mixture constituted by hexamethyldisilazane (1.14 g) and of phenyldichlorosilane (70.84 g), the total disappearance of the disilazane is ascertained by $^1$HNMR spectroscopy. The residual phenyldichlorosilane is then eliminated under high vacuum and a product of formula $(HPhClSi)_2NH$ is then obtained, with a yield of 89% (21.8 g).

Although more stable than the preceding compounds, this product must nevertheless be conserved at $-80°$ C. preferably in an argon atmosphere.

Example 5

Heptamethyldisilazane (20 g) and methyldichlorosilane (52.46 g) are heated to reflux for 6 hours, this ensuring total transilylation of the disilazane (ascertained by $^1$HNMR spectroscopy).

By distillation in vacuo (b.p.$_1$=36° C.), a product of formula (HMeClSi)$_2$N—Me is then isolated with a yield of 94% (20.1 g). Its structure is confirmed by the spectroscopic data. This disilazane is also conserved in an argon atmosphere at −20° C., although it is much more stable than its non N-methylated homologue.

What is claimed is:

1. A compound having the formula:

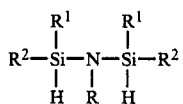

wherein,

R is selected from the group consisting of hydrogen, a hydrocarbon radical, a hydrocarbon radical substituted with a functional group and a group of the formula:

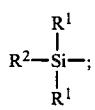

R$^1$ is selected from the group consisting of a hydrocarbon radical and a hydrocarbon radical substituted with a functional group;

R$^2$ is a halogen;

R$^2$ may also be OR when R is a hydrocarbon radical; and

R$^2$ may be NRR$^1$ when R and R$^1$ are both hydrocarbon radicals.

2. The compound of claim 1 wherein R$^2$ is chlorine.

3. The compound of claim 1 wherein R is selected from the group consisting of hydrogen and a hydrocarbon radical selected from the group consisting of an alkyl of 1-4 carbon atoms and an alkenyl of 1-4 carbon atoms.

4. The compound of claim 1 wherein R$^1$ is a hydrocarbon radical selected from the group consisting of an alkyl of 1-4 carbon atoms and an alkenyl of 1-4 carbon atoms.

5. The compound of claim 2 wherein R is selected from the group consisting of hydrogen and a hydrocarbon radical selected from the group consisting of an alkyl of 1-4 carbon atoms and an alkenyl of 1-4 carbon atoms.

6. The compound of claim 5 wherein R$^1$ is a hydrocarbon radical selected from the group consisting of an alkyl of 1-4 carbon atoms and an alkenyl of 1-4 carbon atoms.

7. The compound of claim 2 wherein R$^1$ is methyl and R is hydrogen.

8. The compound of claim 2 wherein R$^1$ is methyl and R is methyl.

9. The compound of claim 2 wherein R$^1$ is vinyl and R is hydrogen.

10. The compound of claim 2 wherein R$^1$ is vinyl and R is methyl.

11. The compound of claim 2 wherein R$^1$ is ethyl and R is hydrogen.

12. The compound of claim 2 wherein R$^1$ is phenyl and R is hydrogen.

* * * * *